US012618052B2

(12) United States Patent
Rathi et al.

(10) Patent No.: US 12,618,052 B2
(45) Date of Patent: May 5, 2026

(54) ENZYME COMPOSITION TO REDUCE GLUCOSE UPTAKE WITHOUT COMPROMISING TASTE

(71) Applicant: Advanced Enzyme Technologies Ltd., Maharashtra (IN)

(72) Inventors: Vasant Laxminarayan Rathi, Yorba Linda, CA (US); Abhijit Rathi, Maharashtra (IN); Swati Jadhav, Maharashtra (IN)

(73) Assignee: Advanced Enzyme Technologies Ltd., Maharashtra (IN)

( * ) Notice: Subject to any disclaimer, the term of this patent is extended or adjusted under 35 U.S.C. 154(b) by 442 days.

(21) Appl. No.: 18/373,125

(22) Filed: Sep. 26, 2023

(65) Prior Publication Data

US 2025/0101388 A1     Mar. 27, 2025

(51) Int. Cl.
*C12N 9/10* (2006.01)
*A23L 33/20* (2016.01)

(52) U.S. Cl.
CPC ............ *C12N 9/1051* (2013.01); *A23L 33/20* (2016.08); *C12Y 204/0114* (2013.01)

(58) Field of Classification Search
CPC . C12N 9/1051; C12Y 33/20; C12Y 204/0114; A23L 33/20
See application file for complete search history.

(56) References Cited

U.S. PATENT DOCUMENTS 7,182,954 B1 * 2/2007 Cote ...................... A23K 50/75
514/35

OTHER PUBLICATIONS

EFSA CEP Panel, Scientific Opinion on the safety evaluation of the food enzyme alternansucrase from Leuconostoc citreum strain NRRL B-30894. EFSA Journal 2021;19(1):6367, 10 pp. (Year: 2021).*

Azaïs-Braesco, V. et al., "A review of total added sugar intakes and dietary sources in Europe," Nutrition Journal, 2017, vol. 16, No. 6, pp. 1-15, DOI: 10.1186/s12937-016-0225-2.

Breda, J. et al., "The importance of the World Health Organization Sugar Guidelines for Dental Health and Obesity Prevention," Caries Research, 2018, vol. 53, No. 2, pp. 149-152, DOI: 10.1159/000491556.

Brodkorb, A. et al., "INFOGEST static in vitro simulation of gastrointestinal food digestion," Nature Protocols, 2019, vol. 14, pp. 1-24, DOI: 10.1038/s41596-018-0119-1.

Giri, B. et al., "Chronic hyperglycemia mediated physiological alteration and metabolic distortion leads to organ dysfunction, infection, cancer progression and other pathophysiological consequences: An update on glucose toxicity," Biomedicine and Pharmacotherapy, 2018, vol. 107, pp. 306-328, DOI: 10.1016/j.biopha.2018.07.157.

Gulati, S. et al., "Sugar Intake, Obesity, and Diabetes in India," Nutrients, 2014, vol. 6, No. 12, pp. 5955-5974, DOI: 10.3390/nu6125955.

Molina, M. et al., "A specific oligosaccharide-binding site in the alternansucrase catalytic domain mediates alternan elongation," Journal of Biochemistry, 2020, vol. 295, No. 28, pp. 9474-9489, DOI: 10.1074/jbc.RA120.013028.

Ricciuto, L. et al., "Sources of Added Sugars Intake Among the U.S. Population: Analysis by Selected Sociodemographic Factors Using the National Health and Nutrition Examination Survey 2011-18," Frontiers in Nutrition, 2021, vol. 8, No. 687643, pp. 1-13, DOI: 10.3389/fnut.2021.687643.

Rippe, J. M. et al., "Relationship between Added Sugars Consumption and Chronic Disease Risk Factors: Current Understanding," Nutrients, 2016, vol. 8, No. 697, pp. 1-19, DOI: 10.3390/nu8110697.

U.S. Department of Agriculture and U.S. Department of Health and Human Services, "Dietary Guidelines for Americans 2020-2025," Dec. 2020, 164 pages.

World Health Organization, "Guideline: Sugars intake for adults and children," 2015, 59 pages.

* cited by examiner

*Primary Examiner* — Ruth A Davis
(74) *Attorney, Agent, or Firm* — Brooks Kushman P.C.

(57) ABSTRACT

A method allows people to not compromise on the taste and flavor of sugar-containing foods and beverages, while reducing the net effect of the sugar in the body. The method may include oral consumption of the enzyme alternansucrase to convert up to 90% of consumed sucrose and other carbohydrates into a carbohydrate complex of undigestible or slowly digestible α-1, 3 and α-1, 6 glucan fibers in the gastrointestinal tract. These glucan fibers have the properties of dietary fibers and a degree of polymerization ranging from 3 to greater than 100. The methods may aid in glucose control, reduce insulin resistance and support healthy glucose homeostasis in diabetic and pre-diabetic conditions. It may promote healthy gut bacteria and improve bowel movements to benefit overall digestive health. It may also be applied to obesity control by reducing blood glucose and, through the production of fiber, blood lipid levels, which supports cardiovascular health.

14 Claims, 6 Drawing Sheets

ENZYME COMPOSITION TO REDUCE GLUCOSE UPTAKE WITHOUT COMPROMISING TASTE

TECHNICAL FIELD

The present application is generally related to an enzyme composition configured to reduce glucose uptake without compromising taste.

BACKGROUND

Carbohydrates are a major food component, accounting for 45-55% of total calories consumed on average, and are a primary source of energy. Starch and sucrose are key components of dietary carbohydrates, and can cause rapid glucose delivery into the body and high blood glucose rise (glycemic response). Both consistently high glucose levels in the blood and irregular surges in blood glucose levels increase the risk of disease conditions like Type 2 diabetes, obesity, coronary heart disease, stroke, atherosclerotic plaque formation, renal disease, and retinopathy.

Improvements in agriculture and industrial development have made sugar more readily available. As a result, the market is flooded with sweetened products like confections, fruit drinks, beverages, baked goods, and even sauces.

The American Heart Association recommends a limit for added sugars: no more than 100 calories per day for most women (the equivalent of 6 teaspoons) and 150 calories per day for most men (the equivalent of 9 teaspoons). Nevertheless, the US population on average intakes added sugars well above recommended levels; the top two food sources responsible for higher sugar intake being sugar-sweetened beverages and sweet bakery products (Ricciuto et al., 2021).

Various efforts have been made to reduce the glycemic index of sweetened food and drinks. One such effort is the use of complex carbohydrates as a sugar replacement in food and beverages. Enzymes within the class glucosyltransferase can convert easily digestible saccharides like sucrose, maltose, malto-oligosaccharides and glucose into sparingly digestible and undigestible saccharides, such as oligosaccharides and polysaccharides (also known as glucan fibers). When these glucan fibers are consumed, they can cause a lower glycemic response than consumption of the original saccharide from which it was produced.

Patent application EP4087937A1 (Applicant: Evoxx) describes a method of production of alternan-oligosaccharide in a reactor. Alternansucrase produces alternan-oligosaccharides in the presence of sucrose and acceptor molecules (maltose). Fructose is produced as a by-product in this process. Formed alternan-oligosaccharide is effective to promote the growth of beneficial bacteria (Lactobacilli, Bifidobacteria).

Patent application US20180146699A1 (Applicant: Nestle) describes a process of reducing intrinsic sugar content of food materials such as fruit juice or any food comprises fruits. In the food material, enzyme glucosyltransferase converts monosaccharides and/or disaccharides into oligosaccharides and/or polysaccharides. During the manufacturing process, the enzyme glucosyltransferase is used as processing aid in the processing of food products.

U.S. Pat. No. 8,512,739B2 (Cargill) describes a method of the preparation of low glycemic sweetener by reacting sucrose and acceptors (a sugar or a sugar alcohol having free hydroxyl groups at one or more of carbon positions numbers 2, 3 and 6 that can accept a glucose unit from sucrose) in the presence of enzyme glucansucrase. The resulting product contains fructose and various glucose oligosaccharides that has low glycemic index. Low glycemic sweetener can be utilized in various foods and beverages.

U.S. Pat. No. 11,261,264B2 (Nutrition & Biosciences USA 4) describes a synthesis of glucan fibers in sucrose containing food products in the presence of enzyme glucosyltransferase. The soluble fiber composition may be directly used as an ingredient in food or may be incorporated into carbohydrate compositions suitable for use in food applications.

The aforementioned patents and patent applications describe the enzymatic synthesis of sparingly digestible or indigestible saccharides as well as the inclusion of indigestible saccharides or enzymes as processing aids into various food matrices. However, the taste of the food is likely changed by the inclusion of the glucan fibers in the food matrices, impacting the palatability of food matrices. Moreover, recipients with a sensitivity to sugar are limited only to packaged food options with the glucan fiber in the food matrices. And, since it is unknown how long the synthesized saccharides will persist in any dietary matrices over time, research would need to be conducted on each food matrices, further limiting the availability of more food options to those who desire or need reduced sugar in food.

Therefore, there is need of a method that enables people to not compromise on the taste and flavor of sugar-containing foods or beverages and still reduce the net effect of the sugar in the body.

There is also need of a method to lower the glycemic index of food without interfering in conventional food manufacturing processes.

There is also a need of a method that can give consumers a variety in their food choices.

SUMMARY

One or more embodiments disclosed herein addresses one or more of these needs by the application of alternansucrase to convert sucrose from sucrose-containing foods to glucan fibers in in-vitro simulated gastrointestinal conditions.

Advantageously, the applicant discovered that alternansucrase converts in the gastrointestinal tract sucrose and other carbohydrates into carbohydrate complex of undigestible and/or slowly digestible α-1, 3 and α-1, 6 glucan fibers.

Advantageously, the applicant discovered that alternansucrase converts up to 90% of consumed sucrose and other carbohydrates into a carbohydrate complex of undigestible and/or slowly digestible α-1, 3 and α-1, 6 glucan fibers in gastrointestinal tract within 5 minutes to 2 hours.

Advantageously, the applicant discovered that oral administration of enzyme alternansucrase reduces the spike in blood sugar levels that would otherwise occur after consumption of sucrose or sucrose containing foods.

Advantageously, the applicant discovered that in gastrointestinal tract alternansucrase forms a carbohydrate complex of undigestible and/or slowly digestible α-1,3 and α-1,6 glucan fibers with a degree of polymerization ranging 3 to greater than 100 after consuming sucrose or a sucrose-containing foods.

Advantageously, the applicant discovered that carbohydrate complex contains dietary fibers that are resistant to intestinal digestion.

One or more embodiments disclose a method that allows people to not compromise on the taste and flavor of sugar containing foods and beverages, while still reducing the net effect of the sugar in the body.

One or more embodiments disclose a method for converting in the gastrointestinal tract sucrose and other carbohydrates into carbohydrate complex of undigestible and/or slowly digestible α-1,3 and α-1,6 glucan fibers. One or more methods comprise oral administration of the enzyme alternansucrase before during or after the consumption of sucrose or sucrose containing foods.

One or more methods relate to the oral consumption of the enzyme alternansucrase to convert up to 15-90% of consumed sucrose and other carbohydrates into a carbohydrate complex of undigestible and/or slowly digestible α-1, 3 and α-1, 6 glucan fibers within 5 minutes to 2 hours in the gastrointestinal tract.

One or more methods reduce the spike in blood sugar levels that would otherwise occur after consumption of sucrose or sucrose-containing foods.

In one aspect, at least 50% of the formed glucan fibers contain dietary fibers.

In another aspect, formed glucan fibers have a range of degree of polymerization from 3 to greater than 100.

One or more methods produce a carbohydrate complex of undigestible and/or slowly digestible α-1, 3 and α-1, 6 glucan fibers that also possess prebiotic properties and control enteric bacterial pathogens in gastrointestinal tract. These fibers may effectively eradicate *Salmonella* species, *Clostridia perfringens*, enteropathogenic and *Escherichia coli* and further promotes the growth and colonization of beneficial bacteria population (*Bifidobacterium* spp. and *Lactobacillus* spp.) in the gastrointestinal tract.

One or more methods aid in glucose control, reduce insulin resistance and support healthy glucose homeostasis in diabetic and pre-diabetic conditions. One or more methods also support overall digestive health by producing glucan fiber to promote the growth of healthy gut bacteria and improve bowel movements.

One or more methods indicate obesity control by reducing the blood glucose and, through the production of fiber, blood lipid levels. Reduction in blood lipid level can also support the cardiovascular health and prevent arteriosclerosis.

DETAILED DESCRIPTION

Figure 1:
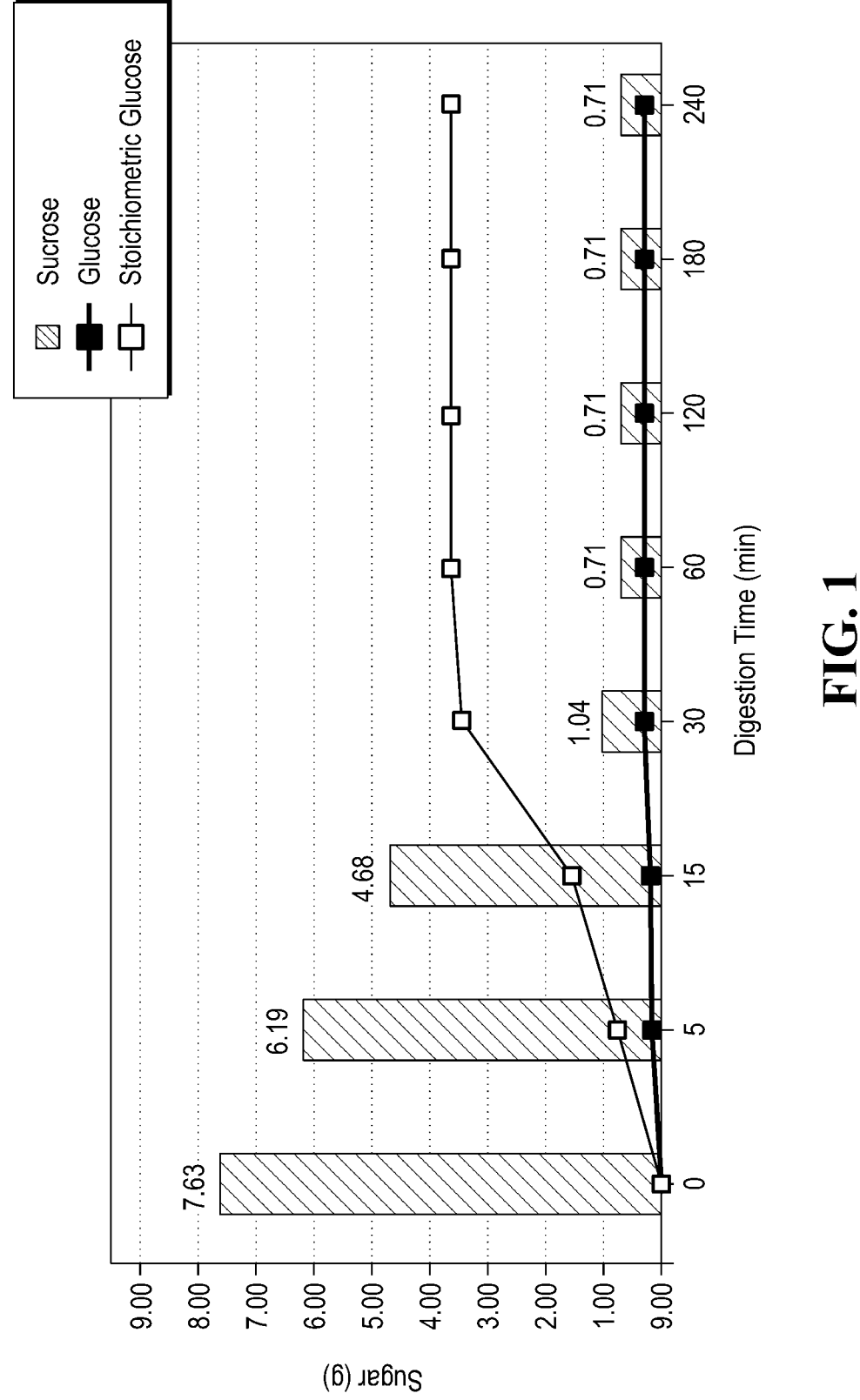
FIG. 1 depicts a graph showing sucrose reduction in the presence of alternansucrase under simulated in-vitro gastrointestinal conditions.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

One aspect of the present invention is directed towards a method that allows people to not compromise on the taste and flavor of sugar-containing foods and beverages, while still reducing the net effect of the sugar in the body.

In one embodiment of the present invention, the enzyme alternansucrase converts in the gastrointestinal tract sucrose and other carbohydrates into a carbohydrate complex of undigestible and/or slowly digestible α-1,3 and α-1,6 glucan fibers. The method comprises orally administration of enzyme alternansucrase before, during or after the consumption of sucrose or sucrose containing foods.

In one or more embodiment of the invention, oral administration of enzyme alternansucrase reduces the spike in blood sugar levels that would otherwise occur after consumption of sucrose or sucrose-containing foods.

The alternansucrase utilizes easily digestible saccharides (sucrose and, under certain conditions, maltose, lactose, raffinose, glucose, xylose, and fructose) and forms a carbohydrate complex of undigestible and/or slowly digestible α-1,3 and α-1,6 glucan fibers (gluco-oligomers and gluco-polymers) in the gastrointestinal tract.

The name alternansucrase is due to the enzyme's ability to convert sucrose into gluco-oligomers or gluco-polymers of alternating α-1, 3 and α-1,6 linkages named "alternan" (Molina et. al., 2020). Alternansucrase hydrolyses sucrose and forms fructose and glucose during the initial stage of the reaction. In this whole process, an acceptor initiates the glucan chain formation. The elongation process is driven by the addition of glucosyl residues at the non-reducing end of previously formed acceptors. Alternansucrase makes high and low molecular weight α-1,3 and α-1,6 glucan fibers; where the acceptor molecule drives the length and nature of the formed glucan fiber.

Acceptors are template sugar molecules to which alternansucrase transfers the glucose unit. Acceptor molecules determine the outcome of the alternansucrase reaction and the kind of products after the sucrose hydrolysis. Alternansucrase utilizes carbohydrate acceptor molecules like maltose, glucose, fructose, arabinose, mannose, leucrose, maltodextrins, maltitol, nigerose, panose, stachyose, kojibiose, isomaltose, isomaltotriose, cellobiose, raffinose, melibiose, lactose, and gentiobiose and produces various types of alpha glucan fibers (gluco-oligomers and gluco-polymers) in the body, depending on the nature and concentration of the acceptor molecules present in the meal.

Alternansucrase for use herein may be obtained from *Leuconostoc mesenteroides, Leuconostoc citreum*, or *Streptococcus mutans*.

Alpha glucan fibers include a large group of liner or branched gluco-oligomers or gluco-polymers that are composed of a glucose moieties joined via α-1,3 and α-1,6 glycosidic linkages. The primary factor used to categorize glucan fiber into gluco-oligomers and gluco-polymers is degree of polymerization.

In one embodiment, the method comprises the conversion in the gastrointestinal tract sucrose and other carbohydrates into a carbohydrate complex of undigestible and/or slowly digestible α-1, 3 and α-1, 6 glucan fibers wherein the degree of polymerization of glucan fiber ranging from 3 to greater than 100.

Degree of polymerization (DP) is defined as a number of monomer units (sugar molecules) present in the chain of carbohydrates. The alpha glucan fibers with <30 DP are classified as gluco-oligomers while the alpha glucan fibers with >30 DP are classified as gluco-polymers. The degree of polymerization and the types of bonds present in the glucan chain decide the digestibility of the carbohydrate in the human gastrointestinal tract. Degree of polymerization may vary with the concentrations and the relative ratio of sucrose and acceptor in alternansucrase-catalyzed reaction. The reaction product is composed of a mixture of gluco-oligomers and gluco-polymers having different degrees of polymerization. At a relatively high sucrose:acceptor ratio, higher degree of polymerization is achieved. In contrast, at a low sucrose:acceptor ratio, the predominant reaction product is of lower degree of polymerization.

In one embodiment, administration of alternansucrase converts the sucrose into carbohydrate complex of undigestible and/or slowly digestible gluco-oligomers wherein degree of polymerization ranging from 3 to 30.

In one embodiment, administration of alternansucrase converts the sucrose into carbohydrate complex of undigestible and/or slowly digestible gluco-polymers wherein degree of polymerization ranging 30 to 100 or more than 100.

In one embodiment, administration of alternansucrase converts the sucrose into a carbohydrate complex of gluco-oligomers and gluco-polymers wherein carbohydrate complex contains between 5-60% gluco-oligomers and 20-95%. gluco-polymers.

In an embodiment, alternansucrase converts sucrose and other carbohydrate into a carbohydrate complex of undigestible and/or slowly digestible α-1,3 and α-1, 6 glucan fibers in the gastrointestinal tract of degrees of polymerization (DP) ranging from 3 to greater than 100. In the first 15 minutes of gastrointestinal digestion, 57% of the glucan fibers were in DP ranging from 3-10, 24% were ranging from 51-100, and 19% were in greater than 100 range. After two hours of gastrointestinal digestion, 40% of the glucan fibers were in DP ranging from 51 and 100, whereas 56% had DP values ranging greater than 100. DP value of the invention has been analyzed with GPC-RI (Gel permeation chromatography with refractive index detection) method. GPC-RI method is summarized in Example 2.

In an embodiment, the carbohydrate complex containing glucan fibers is formed in gastrointestinal conditions with a higher degree of polymerization and with α-1,3 and α-1,6 bonds that are resistant to digestion and have the physiological effect of reducing the post-prandial glucose level.

In one embodiment of the invention, oral consumption of the enzyme alternansucrase converts 15-90% of consumed sucrose and other carbohydrates into carbohydrate complex of undigestible and/or slowly digestible α-1,3 and α-1,6 glucan fibers within 5 minutes to 2 hours in the gastrointestinal tract.

In an embodiment, alternansucrase converts in the gastrointestinal tract sucrose and other carbohydrate into a carbohydrate complex of undigestible and/or slowly digestible α-1,3 and α-1,6 glucan fibers wherein at least 50% of the formed glucan fibers contain dietary fibers and are resistant to digestion. Formed glucan fibers in the invention possess prebiotic properties and control enteric bacterial pathogens in gastrointestinal tract. Additionally, they are effective in controlling *Salmonella* species, *Clostridia perfrin*, and enteropathogenic *Escherichia coli* and promote the growth and establishment of populations of beneficial bacteria (*Bifidobacterium* spp. and *Lactobacillus* spp.) in the gastrointestinal tract. (U.S. Pat. No. 7,182,954B1).

In an embodiment of the invention, alternansucrase forms 0.5 to 2.5 gm dietary fiber per 10 gm of sucrose after consumption of any form and quantity of sucrose or sucrose containing foods.

Generally, dietary fibers are produced from plants and are resistant to enzymatic digestion. Dietary fibers include the polymers of cellulose, non-cellulosic polysaccharides (hemicellulose, pectic materials, gums, and mucilages) and non-carbohydrate compound (lignin). Soluble dietary fibers are more readily accessed and utilized by microbiota than insoluble dietary fibers due to their solubility. Dietary fibers lower the glucose spike in plasma. Dietary fibers affect microbial ecology and boost the production of important microbial metabolites, such as health promoting short-chain fatty acids (SCFAs). Moreover, dietary fibers improve digestion, ease constipation, reduce inflammation, and guard against cancer and cardiovascular diseases. Dietary fibers also increase insulin sensitivity and promote weight loss by decreasing eating frequency. A fiber's utility depends on a number of factors, including but not limited to fiber length, and the nature of the bonds present in fibers.

In an embodiment of the invention, the method comprises oral administration of alternansucrase to convert sucrose and other carbohydrate molecules into a carbohydrate complex of α-1,3 and α-1,6 glucan fibers wherein the enzyme alternansucrase can be consumed before, during or after the consumption of sucrose-containing foods. Sucrose-containing foods can be of any concentration or form of sucrose. Sucrose-containing foods include juice, juice concentrate, ice cream, chocolate, sweets, beverages, soft drinks, frozen dairy desserts and mixes, jams, jellies, candy bars, chocolates, fudge, sweet sauces, toppings, syrups, corn syrup, maple sweet sauces toppings cake, puddings, biscuits, pastries, tarts, confectionary items, fruits and juices, processed food, fast food, tea, coffee, cold drinks, or any form of dessert and foods with added sugar.

In an embodiment of the invention, alternansucrase converts sucrose and other carbohydrates into a carbohydrate complex of undigestible and/or slowly digestible α-1,3 and α-1, 6 glucan fibers wherein the enzyme alternansucrase works in gastrointestinal pH, e.g., 2 to 4.

In an embodiment, enzyme alternansucrase can be administered in any dosage form including tablets, capsules, powder, lozenges, pastilles, or a liquid.

In an embodiment, alternansucrase is orally administered in an amount ranging 0.01 mg to 5000 mg.

In an embodiment, alternansucrase aids in glucose control, reduces insulin resistance, and supports healthy glucose homeostasis in diabetic and pre-diabetic conditions. The method also supports overall digestive health by producing fiber to promote the growth of healthy gut bacteria and improve bowel movements. The method also has indications in obesity control by reducing blood glucose and through the production of fiber, blood lipid levels. This reduction in blood lipid level can also support the cardiovascular health and prevent arteriosclerosis.

EXAMPLES

Examples are set forth herein below and are illustrative of different amounts and types of reactants and reaction conditions that can be utilized in practicing one or more embodiment.

Example 1: Sucrose Reduction by Alternansucrase Under INFOGEST Simulated In-Vitro Gastrointestinal Conditions Sucrose reduction by alternansucrase was studied under simulated in-vitro conditions using the INFOGEST static model. This model is widely accepted as a global standard method for performing digestion reactions.

The INFOGEST static digestion model encompasses first an oral phase (2 min), second a gastric phase (2 h) and finally, an intestinal phase (2 h). In the oral phase, food (10 g) was mixed with simulated salivary fluid (1.25×8 mL), calcium chloride dihydrate (0.3 M, 50 μL), and amylase (1500 U in final volume) and the final volume was adjusted to 20 mL with distilled water. The mixture was incubated at 37±2° C., 100 rpm for 2 min. For the gastric phase, simulated gastric fluid (1.25×16 mL), calcium chloride dihydrate (0.3 M, 10 μL) were mixed with the solution from the oral phase (20 mL), and the pH was adjusted to 3 with 5M hydrochloric acid solution. Pepsin (2000 U/mL in final volume) was added to the mixture, and the final volume was adjusted to 40 mL with distilled water. The gastric mixture was incubated at 37±2° C., 100 rpm for 2 h. For the intestinal phase, simulated intestinal fluid (1.25×, 16 mL), calcium chloride dihydrate (0.3 M, 80 μL) were mixed with the solution from the gastric phase (40 mL), and pH was adjusted to 7 with 5M sodium hydroxide (NaOH) solution. Pancreatin (8000 U/mL in final volume) and bile salts (10 mM in final volume) were added to the mixture, and the final volume was adjusted to 80 mL with distilled water. The resulting mixture was incubated for 2 hours at 37±2° C. and 100 rpm (Brodkorb et al., 2019).

Digestion of sucrose (Sigma S9378-500G) in the presence of alternansucrase was studied under gastro-intestinal conditions as described above. Alternansucrase (20-30 mg/g of sucrose) was added in the digestion reaction. The reaction progress was monitored by taking aliquots at 0 min, 5 min, 15 min, 30 min, 60 min, 120 min, 180 min and 240 min. Samples were heated at 99° C. for 10 min for deactivation of an enzyme followed by HPLC analysis. Analysis was performed using Shodex Asahipak NH2-P with 75% acetonitril as mobile phase at 1 ml/min flow rate and RI detector. FIG. 1 shows that the enzyme could utilize sucrose as a substrate under gastro-intestinal conditions. Sucrose reduction was 18.87% within first 5 min of reaction, which further reduced to 86.36% within 30 min of reaction. At the end of gastric phase, the sucrose reduction was up to 90.69%. Further, till 240 min of gastrointestinal digestion, the reaction showed saturation phase with the reduction of 90.69% of sucrose.

FIG. 1 depicts a graph showing sucrose reduction in the presence of alternansucrase under simulated in-vitro gastrointestinal conditions.

Moreover, the amount of free glucose formed was negligible during and after the reaction. According to stoichiometry, 1 g of sucrose should completely hydrolyze to produce 0.525 g of free glucose, however in this case under gastrointestinal conditions; alternansucrase converts sucrose into fiber preventing the release of free glucose.

Example 2: Conversion of Sucrose into Glucan Fibers by Alternansucrase Under INFOGEST Simulated In-Vitro Gastrointestinal Conditions Digestion of sucrose (Sigma S9378-500G) was carried out using INFOGEST simulated gastrointestinal conditions. INFOGEST model is described in Example 1.

Gel permeation chromatography-Refractive index (GPC-RI) method was used to analyze the degree of polymerization of formed glucan fibers. The HPLC was equipped with a Shodex OHpak SB-802.5HQ column with a RI detector; water was utilized as the mobile phase, and the flow rate was kept constant at 1 ml/min throughout the process. The sample was pre-treated with solvent to precipitate the glucan fibers from the reaction mixture and analyzed using the GPC-HPLC technique. Column calibration was performed using appropriate molecular weight standards run under the same analytical conditions. The samples were analyzed to obtain chromatograms, where each peak representing a group of glucan fibers with similar molecular weights. The molecular weights were calculated from the retention times of the various peaks using a standard curve. The chain length of the glucan fibers generated in the reaction was used to categorize them.

Figure 2:
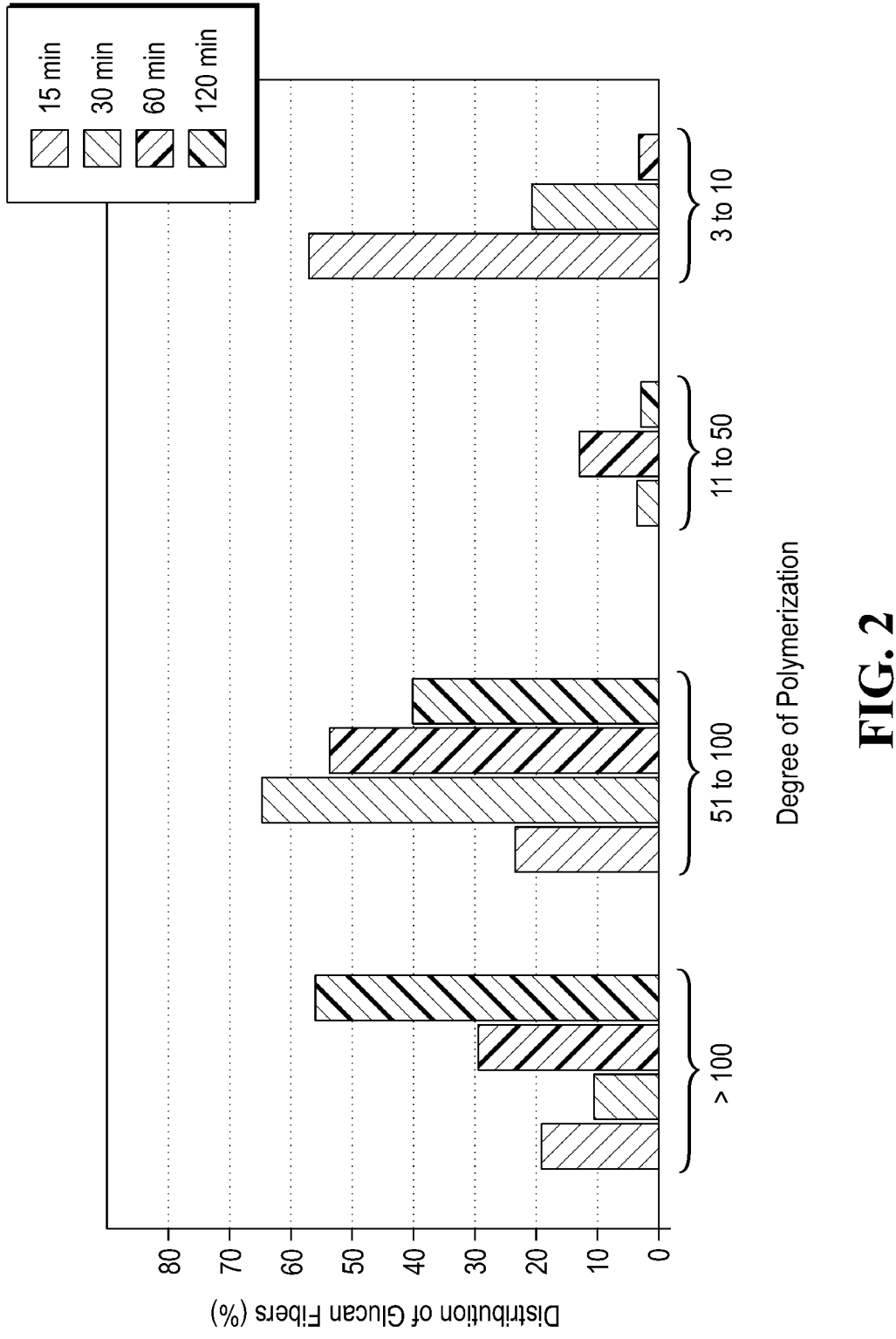
FIG. 2 depicts a graph showing the degree of polymerization of formed glucan fibers in the presence of alternansucrase under simulated in-vitro gastrointestinal conditions.

FIG. 2 depicts the results of this experiment, which reveal that the molecular weight distribution of glucan fibers vary with reaction time. During the first 15 minutes of gastrointestinal digestion, 57% of the glucan fibers were of DP ranging from 3-10, 24% of glucan fibers were of DP ranging from 51-100, and 19% glucan fibers were DP greater than 100. After 2 hours of gastrointestinal digestion, 56% of the glucan fibers had a DP more than 100, while 40% had a DP between 51 and 100. The results demonstrated that alternansucrase has the potential to initiate and elongate glucan fibers from sucrose in gastrointestinal digestion conditions.

FIG. 2 depicts a graph showing the degree of polymerization of glucan fibers formed from sucrose in the presence of alternansucrase under simulated in-vitro gastrointestinal conditions.

Example 3: Resistance of the Glucan Fibers Formed by Alternansucrase to Pancreatin and Rat Intestinal Extract (RIE)

Sucrose (Sigma S9378-500G) digestion was studied in the presence of alternansucrase under simulated in-vitro gastrointestinal conditions as described in the Example 1. At the end of the gastric phase, the glucan fibers were purified by adding ethanol (1:9 v/v ratio) and kept them overnight to precipitate; the precipitated fibers were then separated by centrifugation and drying. The dried fibers were enzymatically hydrolyzed by digestive enzymes to determine their digestion resistance during the intestinal phase. To obtain a 1% (w/v) solution, the fibers were reconstituted in phosphate buffer (pH 6.9, 20 mM). Pancreatin (Sigma, 8× USP) was dissolved in 20 mM phosphate buffer pH 6.9 and 6 mM sodium chloride (100 mg/ml). Both solutions were mixed in a 1:1 (v/v) ratio and the reaction was run at 37° C. for 120 minutes to mimic intestine digestion. Samples were taken at 0, 60, and 120 minutes and analyzed using the GOD-POD (Arkray glucose kit) assay to determine the amount of free glucose liberated during the reaction.

TABLES

Table 1 demonstrates that the negligible amount of glucose was released after the reaction of fibers with pancreatin for 120 min, showing fiber resistance to the catalytic action of pancreatin.

Table 2 demonstrates that the action of rat intestine extract (RIE) hydrolyzed all carbohydrate samples except the glucan fibers, and released free glucose.

TABLE 1

Free glucose liberated from the fibers
during the reaction with pancreatin.

| | Free glucose released (µg) | | |
| --- | --- | --- | --- |
| Sample | 0 min | 60 min | 120 min |
| Fibers (5000 µg) | 14.8 | 20.4 | 24.1 |

TABLE 2

Hydrolysis of different carbohydrates by rat intestinal extract (RIE)

| | Free glucose released with respect to theoretical glucose (%) | | |
| --- | --- | --- | --- |
| Carbohydrate source | 0 min | 60 min | 120 min |
| Sucrose | 7.1 | 21.2 | 56.7 |
| Maltose | 58.3 | 88.3 | 91.8 |
| Starch | 8.9 | 74.5 | 91.9 |
| Fiber | 0.4 | 2.1 | 3.0 |

It was observed that glucose released from sucrose, maltose and starch was equivalent to 56.7%, 91.8% and 91.9% of its stoichiometric glucose values, respectively. The glycosidic bonds in these substrates were cleaved by the carbohydrases present in RIE, and released free glucose within 120 minutes. The glucan fibers, on the other hand, were unaffected by RIE treatment. The glucan fibers were stable under small intestinal digestion conditions, indicating that they have dietary fiber potential.

Example 4: Dietary Fibers Potential of Carbohydrate Complex Formed by Alternansucrase Under Simulated In-Vitro Gastrointestinal Conditions Digestion of simple sugar (sucrose) and complex food (diskette) was carried out using the method described in Example 1. The Megazyme (Total Dietary Fiber-TDF) Kit was used to assess the dietary fiber potential of the produced glucan fibers. The TDF analysis was carried out in accordance with the manufacturer's protocols. To solubilize digestible organic content, a sample (1 g) was sequentially digested with amylase, protease, and glucoamylase (pH adjusted to 4.5) in the presence of MES-Tris buffer (pH 8.0, 50 mM). Following that, the sample was combined with 1:4 volumes of 78% ethanol to precipitate dietary fibers and kept at room temperature (25° C.) for 60 minutes before being filtered through a Gooch crucible containing filter aid (Celite). The solids obtained as filter cake was dried at 105° C. and the dry weight (after negating residual protein and ash) indicated the sample's dietary fiber content.

Table 3 demonstrates that the total dietary fibers obtained from sucrose by the reaction of alternansucrase was 10% of the original food material. In the case of diskette, it was 6.29% and 7.63% when the digestion occurred in the absence and presence of alternansucrase, respectively. Hence, the alternansucrase can increase the dietary fiber potential of the diskette by 21.30%.

TABLE 3

Total dietary fiber content of glucan fibers formed
from sucrose and diskette by alternansucrase under
simulated in-vitro gastrointestinal conditions.

| Food used | Alternansucrase added | Food (g) | Weight of ethanol precipitated solids (g) | Total dietary fiber (g) |
| --- | --- | --- | --- | --- |
| Simple sugar | No | 10 | 0 | 0.000 |
| (sucrose) | Yes | 10 | 1.995 | 0.992 |
| Complex food | No | 10 | 4.886 | 0.629 |
| (diskette) | Yes | 10 | 5.642 | 0.763 |

Example 5: Sucrose Reduction in Different Foods (Solid and Liquid) by Alternansucrase Under In-Vitro Simulated Gastrointestinal Conditions Under INFOGEST simulated in-vitro gastrointestinal conditions digestion of various foods such as liquid foods (cold drinks-CD 1-Sprite, CD 2-Pepsi, CD 3-Fanta, CD 4-Coca cola, beverages-BV 1-milk tea BV 2-milk coffee, BV 3-black coffee, BV 4-soy milk, fruit juices-FJ 1-mango juice, FJ 2-apple juice, FJ 3-pomegranate juice) and solid foods (sponge cake, ice-cream, pastry, biscuit) was carried out as described in Example 1. The alternansucrase dose was kept as 10-20 mg per 10 gm of food. After 120 min of incubation, the sample was pretreated and analyzed by HPLC to evaluate sucrose reduction. The results demonstrated that alternansucrase could decrease sucrose from both liquid and solid meal matrices (FIG. 3) with no elicitation of free glucose in the digested fraction.

Figure 3:
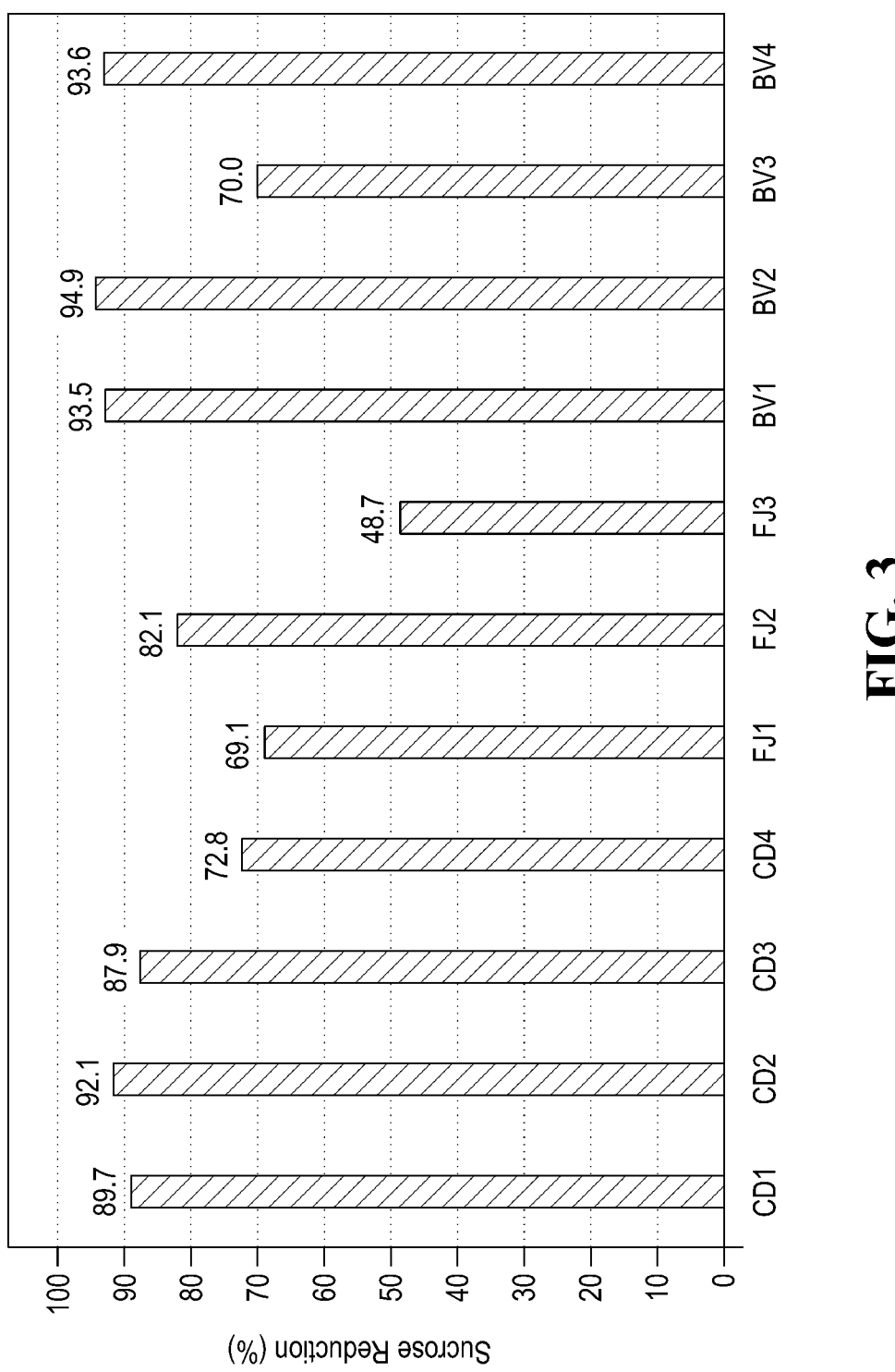
FIG. 3 depicts a graph showing the sucrose reduction in liquid food matrices in the presence of alternansucrase under simulated in-vitro gastrointestinal conditions (CD-Cold drink; FJ-Fruit juice; BV-Beverages).

FIG. 3 depicts a graph showing sucrose reduction of liquid food matrices in the presence of alternansucrase under simulated in-vitro gastrointestinal conditions (CD—Cold drink; FJ—Fruit juice; BV—Beverages)

Figure 4:
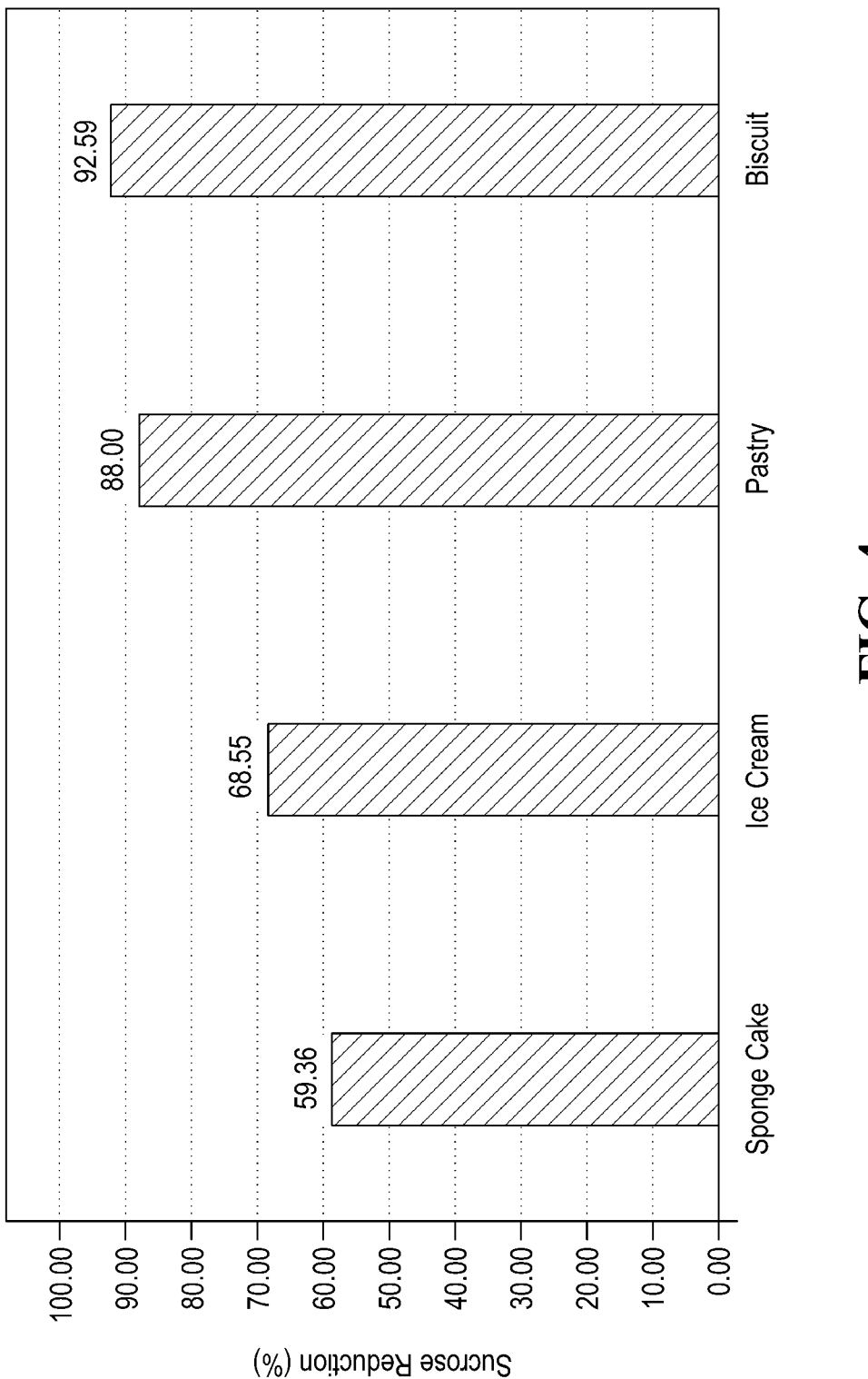
FIG. 4 depicts a graph showing the sucrose reduction in solid food matrices in the presence of alternansucrase under simulated in-vitro gastrointestinal conditions.

FIG. 4 depicts a graph showing sucrose reduction of solid food matrices in the presence of alternansucrase under simulated in-vitro gastrointestinal conditions.

Example 6: Reduction of Sucrose and Other Carbohydrates by Alternansucrase

Alternansucrase reduced sucrose and other carbohydrates at 37° C. and pH 3 (similar to gastric conditions). Lactose (SD Fine 20139.K05), maltose (Merck 1.94941.0251), and raffinose (SRL 51649) were chosen as model carbohydrates since they are commonly present in food matrices (such as milk, grains, and vegetables) with sucrose. The sucrose conversion reaction was carried out as described in example 1 along with the addition of other carbohydrates. In the reaction mixture, 0.16 gm of other carbs and 10 mg enzyme was added for 1 g of sucrose. Reaction was carried out at 37° C. and pH 3.0 in order to mimic the stomach acid environment. Aliquots were taken at 0 minutes, 15 minutes, 30 minutes, 60 minutes, and 120 minutes, and HPLC analysis was performed in accordance with Example 1.

Figure 5:
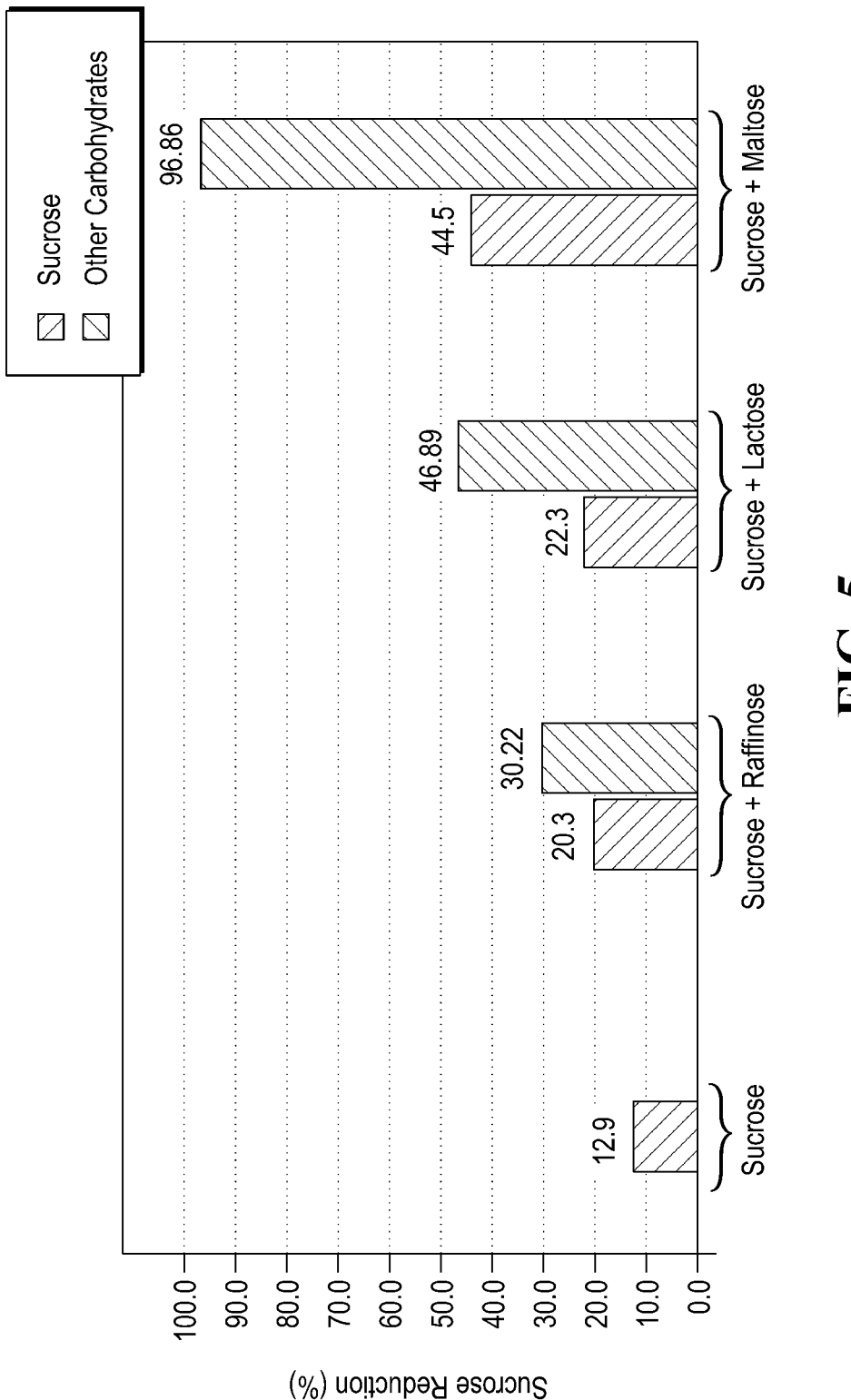
FIG. 5 depicts a graph showing the reduction of sucrose and other carbohydrates at pH 3 (gastrointestinal conditions) by alternansucrase.

FIG. 5 showed that, the sucrose reduction was favored in the presence of other sugars like maltose (44.5% reduction), lactose (22.3% reduction), and raffinose (20.3%) as compared to sucrose alone (12.9% reduction); the order of reaction enhancement by individual sugars was maltose>lactose>raffinose. The results further showed that the sucrose as well as other carbohydrates were converted to fibers by the reaction with alternansucrase as we observed reduction in these sugars without release of glucose in the reaction mixture.

FIG. 5 depicts a graph showing the reduction of sucrose and other carbohydrates by alternansucrase at pH 3.0.

Example 7: Blood Glucose Level Lowering Effect of Alternansucrase in Wistar Rats Blood glucose level lowering effect of alternansucrase was studied in wistar rats (ten males and ten females, in each group: Control and treatment) for 90 days. Alternansucrase was administered by oral gavage with a dose of 1000 mg/kg body weight while the control group was fed with sterile water. Blood glucose levels from the control and treatment groups were compared after 90 days.

Figure 6:
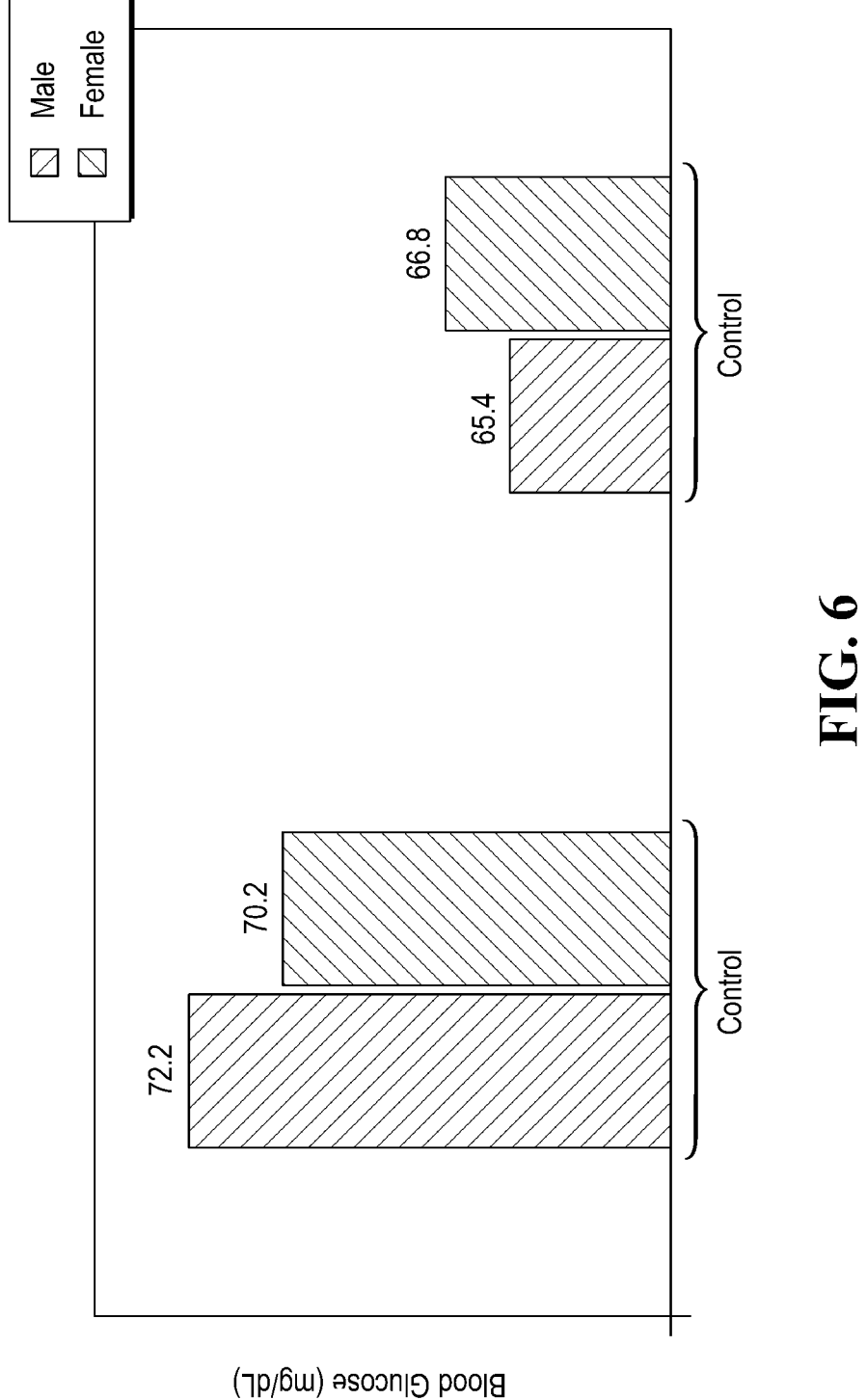
FIG. 6 depicts a graph showing the blood glucose levels of wistar rats males and females without (control) and with (test) administration of alternansucrase for 90 days.

FIG. 6 shows that among the treatment groups of male and female rats had blood glucose levels of 65.40 mg/dL and 66.80 mg/dL respectively, while in control group male and female rats had blood glucose levels of 72.20 mg/dL and 70.20 mg/dL respectively. These results suggest that alternansucrase supplementation resulted in reduction of free glucose by 9.42% (in males) and 4.84% (in females) after 90 days treatment.

FIG. 6 depicts a graph showing blood glucose levels of wistar rat males and females without (control) and with (test) administration of alternansucrase for 90 days.

The foregoing description of the invention has been set merely to illustrate the invention and is not intended to be limiting. Since the modifications of the disclosed embodiments incorporating the spirit and substance of the invention may occur to the person skilled in the art, the invention should be construed to include everything within the scope of the disclosure.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for converting in the gastrointestinal tract sucrose and other carbohydrates into a carbohydrate complex of undigestible and/or slowly digestible α-1,3 and α-1,6 glucan fibers, the method comprising orally administering alternansucrase before, during or after the consumption of sucrose or sucrose-containing foods.

2. The method of claim 1, wherein 15-90% of the consumed sucrose is converted into glucan fibers.

3. The method of claim 1, wherein the conversion to glucan fibers occurs within 5 minutes to 2 hours of oral administration and consumption.

4. The method of claim 1, wherein the carbohydrate complex contains between 5% and 60% gluco-oligomers and between 20% and 95% gluco-polymers.

5. The method of claim 1, wherein the carbohydrate complex is physiologically active or inactive in the body.

6. The method of claim 1, wherein the oral administration of the alternansucrase reduces a spike in blood sugar levels that occurs after consumption of sucrose or sucrose-containing foods.

7. The method of claim 1, wherein at least 50% of the formed glucan fibers contain dietary fibers.

8. The method of claim 1, wherein the carbohydrate complex is composed of undigestible and/or slowly digestible glucan fibers with a degree of polymerization greater than or equal to 3.

9. The method of claim 1, wherein the glucan fibers have a degree of polymerization between 3 and 30.

10. The method of claim 1, wherein the glucan fibers have a degree of polymerization of between 30 and 100 or greater than 100.

11. The method of claim 1, wherein the foods include one or more of the following: juice, juice concentrate, ice cream, chocolate, beverages, soft drinks, frozen dairy desserts, jams, jellies, candy bars, chocolates, fudge, and syrups.

12. The method of claim 1, wherein the alternansucrase catalyzes a transfer of a glucose molecule from a sucrose molecule to a carbohydrate or carbohydrate-derived acceptor molecule.

13. The method of claim 1, wherein the other carbohydrates include one or more of the following: fructose, leucrose, sucrose, maltose, lactose, raffinose, maltitol, panose, nigerose, isomaltose, kojibiose, alternan, and maltoalternan.

14. The method of claim 1, wherein the alternansucrase is orally administered in an amount ranging 0.1 mg to 5000 mg.

\* \* \* \* \*